US009760991B2

(12) United States Patent
Thiruvenkadam et al.

(10) Patent No.: US 9,760,991 B2
(45) Date of Patent: Sep. 12, 2017

(54) SYSTEM AND METHOD FOR IMAGE INTENSITY BIAS ESTIMATION AND TISSUE SEGMENTATION

(71) Applicant: General Electric Company, Schenectady, NY (US)

(72) Inventors: Sheshadri Thiruvenkadam, Bangalore (IN); Rakesh Mullick, Bangalore (IN); Sandeep Kaushik, Bangalore (IN); Hua Qian, Niskayuna, NY (US); Dattesh Shanbhag, Bangalore (IN); Florian Wiesinger, Garching (DE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 22 days.

(21) Appl. No.: 14/786,508

(22) PCT Filed: Apr. 21, 2014

(86) PCT No.: PCT/US2014/034772
§ 371 (c)(1),
(2) Date: Oct. 22, 2015

(87) PCT Pub. No.: WO2014/176154
PCT Pub. Date: Oct. 30, 2014

(65) Prior Publication Data
US 2016/0071263 A1     Mar. 10, 2016

(30) Foreign Application Priority Data

Apr. 22, 2013   (IN) .......................... 1767/CHE/2013

(51) Int. Cl.
*G06K 9/00*   (2006.01)
*G06T 7/00*   (2017.01)
(Continued)

(52) U.S. Cl.
CPC ............ *G06T 7/0012* (2013.01); *A61B 5/055* (2013.01); *A61B 6/032* (2013.01); *A61B 6/037* (2013.01);
(Continued)

(58) Field of Classification Search
None
See application file for complete search history.

(56) References Cited

U.S. PATENT DOCUMENTS

| | | | |
|---|---|---|---|
| 2009/0206838 A1* | 8/2009 | Noterdaeme | G01R 33/56563 324/309 |
| 2011/0208039 A1* | 8/2011 | Guehring | G01R 33/5659 600/410 |

(Continued)

OTHER PUBLICATIONS

S D Wollenweber et al: "Comparison of 4-class and Continuous Fat/Water Methods for Whole-Body, MR-Based PET Attenuation Correction", 2012 IEEE Nuclear Science Symposiwn and Medical Imaging Conference Record (NSS/MIC), Nov. 3, 2012, (Nov. 3, 2012), pp. 3019-3025, XP055134154, ISBN: 978-1-46-732028-3. Abstract p. 3020-p. 3021.

(Continued)

*Primary Examiner* — Shervin Nakhjavan

(57) ABSTRACT

A system and method for estimating image intensity bias and segmentation tissues is presented. The system and method includes obtaining a first image data set and at least a second image data set, wherein the first and second image data sets are representative of an anatomical region in a subject of interest. Furthermore, the system and method includes generating a baseline bias map by processing the first image data set. The system and method also includes determining a baseline body mask by processing the second image data set. In addition, the system and method includes estimating a bias map corresponding to a sub-region in the anatomical region based on the baseline body mask. Moreover, the (Continued)

system and method includes segmenting one or more tissues in the anatomical region based on the bias map.

11 Claims, 4 Drawing Sheets

(51) Int. Cl.
| | |
|---|---|
| *A61B 5/055* | (2006.01) |
| *A61B 6/03* | (2006.01) |
| *A61B 8/13* | (2006.01) |
| *G06T 5/20* | (2006.01) |
| *G06T 7/11* | (2017.01) |
| *G06T 7/12* | (2017.01) |
| *G06T 7/149* | (2017.01) |
| *G06T 7/174* | (2017.01) |
| *G06T 7/136* | (2017.01) |

(52) U.S. Cl.
CPC .................. *A61B 8/13* (2013.01); *G06T 5/20* (2013.01); *G06T 7/11* (2017.01); *G06T 7/12* (2017.01); *G06T 7/136* (2017.01); *G06T 7/149* (2017.01); *G06T 7/174* (2017.01); *G06T 2207/10081* (2013.01); *G06T 2207/10088* (2013.01); *G06T 2207/10104* (2013.01); *G06T 2207/20116* (2013.01); *G06T 2207/30004* (2013.01); *G06T 2207/30024* (2013.01); *G06T 2210/41* (2013.01)

(56) References Cited

U.S. PATENT DOCUMENTS

2013/0079626 A1* 3/2013 Shmatukha .............. A61B 6/03
 600/420
2013/0266198 A1* 10/2013 Pereira .................. G06T 7/0012
 382/131

OTHER PUBLICATIONS

Baowei Fei et al: "An MRI-based attenuation correction method for combined PET/MRI applications", Proceedings of SPEI, vol. 7262, Feb. 26, 2009 (Feb. 26, 2009), pp. 726208-726208-8, XP055134162, ISSN: 0277-786X, DOI: 10.1117/12.813755. Abstract p. 4.

International Search Report and Written Opinion for International Application No. PCT/US2014/034772, mail date Aug. 20, 2014. 12 pages.

* cited by examiner

PRIOR ART  PRIOR ART

SYSTEM AND METHOD FOR IMAGE INTENSITY BIAS ESTIMATION AND TISSUE SEGMENTATION

CROSS-REFERENCE TO RELATED APPLICATIONS

This is a national stage application under 35 U.S.C. §371(c) of prior filed, co-pending PCT Application No. PCT/US14/034772, filed on Apr. 21, 2014, which claims priority to India Provisional Patent Application No. 1767/CHE/2013, filed on Apr. 22, 2013. The aforementioned applications are herein incorporated in their entirety by reference.

BACKGROUND

Embodiments of the present specification relate to imaging, and more particularly to estimation of image intensity bias and segmentation of tissue classes.

In modern healthcare facilities, non-invasive imaging systems are often used for identifying, diagnosing, and treating physical conditions. Medical imaging encompasses different techniques used to image and visualize the internal structures and/or functional behavior (such as chemical or metabolic activity) of organs and tissues within a patient. Currently, a number of modalities of medical diagnostic and imaging systems exist, each typically operating on different physical principles to generate different types of images and information. These modalities include ultrasound systems, computed tomography (CT) systems, X-ray systems (including both conventional and digital or digitized imaging systems), positron emission tomography (PET) systems, single photon emission computed tomography (SPECT) systems, and magnetic resonance (MR) imaging systems.

Over the last few years, use of PET-MR imaging has been gaining momentum. In particular, significant technical advancements have enabled integration of PET and MR imaging solutions. However, MR signals, despite use of multiple contrasts, fail to correlate with PET photon attenuation. Therefore, MR image analysis methods in the form of segmentation of fat-water Dixon images (for example, thresholding based methods, active contour methods, and phase field based methods) and atlas/template registration have been investigated to generate attenuation correction (AC) maps based on tissue classification. Phase-field based methods are similar to the active contour methods. In particular, the phase-field methods provide a closed contour solution and are resilient to image noise when compared to thresholding based methods. However, the phase-field based tissue classification needs to be "tuned" to account for non-homogenous signal intensity distribution across whole body MR images. The inhomogeneity in the signal intensity in the MR images is primarily attributed to radio frequency (RF) transmission and coil sensitivity bias.

Problems associated with the inhomogeneity in the MR images may be substantially mitigated via use of body coil based image data acquisition. Moreover, since the phase-field based methods are relatively insensitive to image signal to noise ratio (SNR), higher encoding efficiency may be achieved via use of surface coil based parallel imaging methods. Also, surface coil based single-breathhold acquisition of high-resolution images may be employed for AC map generation and for anatomical referencing of PET findings. However, use of surface coil based image data acquisition results in large intensity bias in the MR image signal data. Traditional segmentation methods perform poorly in the presence of the large intensity signal bias. Moreover, the coil sensitivity related spatial signal variations associated with surface coil based image data acquisition exacerbate the need for retuning the segmentation techniques. Additionally, these coil sensitivity related spatial signal variations result in tissue segmentation failures even in cases of moderate shading.

BRIEF DESCRIPTION

In accordance with aspects of the present specification, a method for estimating image intensity bias and segmenting tissues is presented. The method includes obtaining a first image data set and at least a second image data set, wherein the first image data set and the second image data set are representative of an anatomical region in a subject of interest. Furthermore, the method includes generating a baseline bias map by processing the first image data set. The method also includes determining a baseline body mask by processing the second image data set. In addition, the method includes estimating a bias map corresponding to a sub-region in the anatomical region based on the baseline body mask. Moreover, the method includes segmenting one or more tissues in the anatomical region based on the bias map.

In accordance with another aspect of the present specification, a system for estimating image intensity bias and segmenting tissues is presented. The system includes a bias estimating and segmenting unit configured to obtain a first image data set and at least a second image data set, wherein the first image data set and the second image data set are representative of an anatomical region, generate a baseline bias map based on the first image data set, determine a baseline body mask based on the second image data set, estimate a bias map corresponding to a sub-region in the anatomical region based on the baseline body mask, and segment one or more tissues in the anatomical region based on the bias map.

In accordance with yet another aspect of the present specification, a system is presented. The system includes a plurality of acquisition subsystems, wherein the plurality of acquisition subsystems is configured to acquire at least a first image data set and a second image data set corresponding to a subject of interest, and wherein the first image data set and the second image data set are representative of anatomically matched image data sets. Additionally, the system includes a processing subsystem including a bias estimating and segmenting unit configured to receive at least the first image data set and the second image data set, generate a baseline bias map based on the first image data set, determine a baseline body mask based on the second image data set, estimate a bias map corresponding to a sub-region in the anatomical region encompassed by the baseline body mask, and segment one or more tissues in the anatomical region based on the bias map.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Systems and methods for the estimation/correction of signal bias and segmentation of tissue classes in magnetic resonance (MR) images presented hereinafter enhance clinical workflow by providing a robust framework for segmentation of magnetic resonance imaging (MRI) data that is resilient to a broad range of image intensity artifacts. In addition, the systems and methods obviate the need for "retuning" segmentation techniques.

Figure 1:
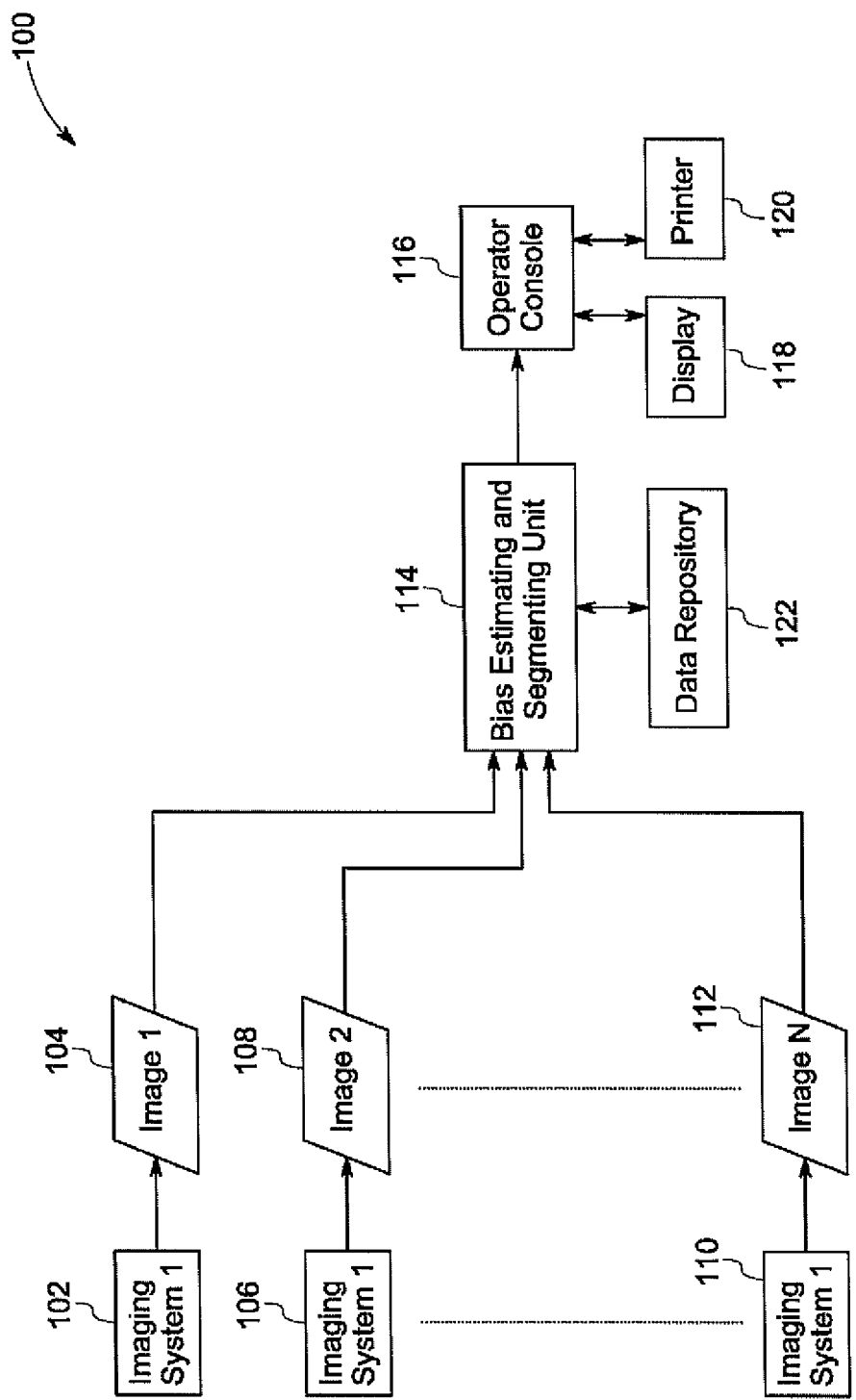
FIG. 1 is a diagrammatical illustration of a system for image intensity bias estimation and tissue segmentation, in accordance with aspects of the present specification.

FIG. 1 is a block diagram of an exemplary system 100 for use in imaging, in accordance with aspects of the present specification. As will be appreciated by one skilled in the art, the figures are for illustrative purposes and are not drawn to scale. The system 100 may be configured to forge a synergy between image data sets acquired via a plurality of imaging systems to enhance the robustness of the estimation/correction of signal bias and the segmentation of the tissue classes corresponding to an anatomical region of interest in a subject of interest, such as a patient (not shown). In particular, the system 100 is configured to use the synergy between anatomically matched image data sets that are representative of the anatomical region in the subject of interest. It may be noted that the anatomically matched image data sets are acquired via different imaging systems. By way of example, the system 100 is configured to use information derived from positron emission tomography (PET) image data and magnetic resonance (MR) image data to estimate and correct any spatial signal bias in the MR image data and segment tissue classes corresponding to the anatomical region being imaged.

Accordingly, the system 100 may be configured to receive a plurality of image data sets that have been acquired via a plurality of image acquisition systems. In one example, the system 100 may be configured to receive a first image data set 104, a second image data set 108 and an $N^{th}$ image data set 112. It may be noted that these image data sets 104, 108, 112 are representative of an anatomical region being imaged in a patient. Moreover, the first image data set 104 may be acquired by a first imaging system 102, while the second image data set 108 may be acquired by a second imaging system 106. Similarly, an $N^{th}$ imaging system 110 may be used to acquire the $N^{th}$ image data set 112. Also, in one example, the first image data set 104 may include MR image data representative of the head of the patient, while the second image data set 108 may include PET image data representative of the head of the patient. Also, the $N^{th}$ image data set 112 may include computed tomography (CT) image data representative of the head of the patient. It may be noted that the term images, image data sets and image volumes may be used interchangeably. Also, in certain embodiments the system 100 may be configured to acquire image data from a computed tomography (CT) imaging system, a positron emission tomography (PET) imaging system, a single photon emission computed tomography (SPECT) imaging system, an ultrasound imaging system, an X-ray imaging system, a magnetic resonance (MR) imaging system, an optical imaging system, or combinations thereof.

The functioning of the system 100 will be described with reference to use of the first image data set 104 that includes MR image data and the second image data set 108 that includes PET image data. However, use of other image data such as, but not limited to, CT image data, ultrasound image data, SPECT image data, and the like is also envisaged.

In the case of imaging via a PET imaging system and a magnetic resonance imaging (MRI) system, it is desirable that minimal time be spent for generation of MR attenuation maps using MRI Dixon fat-water data, thereby warranting use of surface coil based parallel image data acquisition. Unfortunately, use of surface coil based parallel image data acquisition results in a large intensity bias being introduced in the MR images due to surface coil transmission and reception sensitivity profile. Traditional methods for segmenting tissues perform poorly in the presence intensity inhomogeneity or shading across images due to the bias field.

The shortcomings of the currently available techniques are circumvented via use of a bias estimating and segmenting (BES) unit or platform 114. In a presently contemplated configuration, the system 100 includes the BES unit 114, where the BES unit 114 is configured to simultaneously/concurrently estimate and correct any spatial signal bias in the MR image data 104 introduced by radio-frequency (RF) transmission and coils used to acquire the image data. Additionally, the BES unit 114 may be configured to segment one or more tissue classes in MR image data 104.

In accordance with aspects of the present specification, the BES unit 114 may be configured to use a synergy between the MR and PET image data sets 104, 108 to estimate and correct the spatial signal bias and segment the tissue types or classes in the MR image data 104. In particular, the BES unit 114 may be configured to use information derived from the PET image data 108 to "quantify" and enhance the "quality" of shading correction. As will be appreciated, the PET image data 108 is generally unaffected by any RF inhomogeneity. Also, in certain situations, the patient may have metallic objects such as, but not limited to, implants, chemo-ports, and sutures. The PET based body contour is unaffected by the presence of any metallic objects. However, the presence of the metallic objects adversely distorts the MRI body contour due to signal voids created due to the metallic objects.

Accordingly, the BES unit 114 may be configured to use the PET image data 108 to aid in identifying an initial region in the MR image data 104 for bias estimation. By way of example, the BES unit 114 may be configured to process the PET image data 108 to obtain an initial body contour or mask that includes and/or encompasses the anatomical region being imaged. The initial body mask may be referred to as a baseline body mask. The baseline body mask may be used to as a general indicator of a boundary of a region for which the bias is to be estimated. The term body mask may be used to refer to a binary segmentation mask where a pixel has a value of 1 if the pixel lies within a body region and has a value of 0 if the pixel lies outside the body region. Additionally, the term baseline body mask may be used to refer to an initial estimate or contour of the body mask.

Furthermore, the BES unit 114 may also be configured to generate an initial bias map using the MR image data 104 based on the baseline body mask provided by the PET image data 108. More particularly, the MR image data 104 may be processed to determine an estimate of the bias in the region in the MR image data 104 that is encompassed by the baseline body mask. The initial bias map may generally be referred to as a baseline bias map. Also, the initial bias may be referred to as a baseline bias. The term bias map may be used to refer to a map that captures the effects of signal inhomogeneity in MR images, where the signal inhomogeneity manifests itself as a spatially varying shading effect. Furthermore, the term baseline bias map is used to refer to an initial estimate of the bias map.

In one embodiment, the BES unit 114 may be configured to estimate the bias by processing the MR image data 104 via use of a low pass filter, such as a Gaussian filter. In another embodiment, the BES unit 114 may be configured to estimate the initial bias based on coil or scanner calibration data. The scanner calibration data may be generated using calibration data or sensitivity profiles corresponding to the plurality of coils used in the parallel imaging process. In certain other embodiments, the BES unit 114 may instead rely on retrospective non-parametric, non-uniform intensity normalization (N3) and its variant (N4) based methods to estimate the initial bias. However, in certain embodiments, a combination of the low pass filter, the scanner calibration data and the bias field correction map such as a bias field corrected map or a retrospective bias field corrected map may be used to estimate the initial bias.

Consequent to the processing of the MR image data 104 by the BES unit 114, an initial or baseline bias map may be generated. In a similar fashion, subsequent to the processing of the PET image data 108 by the BES unit 114, a baseline body mask may be generated. The baseline body mask may be representative or indicative of initial estimate of the body contour. As previously noted, the baseline body mask may be employed to serve as an indicator of the region that encompasses the anatomical region.

In accordance with aspects of the present specification, the BES unit 114 may be further configured to estimate the bias field from the MR image data 104 based on the baseline bias map and the baseline body mask. Accordingly, the BES unit 114 may be configured to initiate the estimation of the bias in the MR image data 104 corresponding to the region encompassed by the baseline body mask. Following the processing of the MR image data 104 by the BES unit 114, a corrected intensity image may be generated. Moreover, a revised bias map corresponding to the corrected intensity image may also be generated by the BES unit 114. In addition, the BES unit 114 may be configured to generate an updated contour or body mask corresponding to the corrected intensity image. In one example, the BES unit 114 may be configured to simultaneously generate the corrected intensity image, revise the bias map, and update the body mask.

Moreover, in one example, the BES unit 114 may be configured to simultaneously generate the corrected intensity image, revise the bias map, and update the body mask using a two-class phase-field formulation. The two-class phase-field formulation is represented by a spatial membership function "u," with u=0 representing the background and u=1 representing the body mask. In particular, the spatial membership function u is representative of a binary segmentation mask. Also, the two-class phase-field formulation is represented by the term b, where b is representative of the bias. In addition, other parameters in the two-class phase-field formulation related to noise variance, smoothness and sensitivity may be manually set. The PET-derived body mask may be used to understand the level of inhomogeneity in the MR image data 104. The parameters in the two-class phase-field formulation may be varied based on the determined level of inhomogeneity. Furthermore, the two-class phase-field formulation leads to an Euler Lagrange equation and may be a semi-linear partial differential equation (PDE). In addition, the energy of the two-class phase-field formulation may be minimized using descent techniques, such as the steepest descent technique. More particularly, the descent equation may be solved using a finite differences based semi-implicit iterative method in a multi resolution framework. Since the spatial membership function u plays the role of a segmentation mask, the body mask u may be thresholded to maintain the value of u in $\{0, 1\}$.

Furthermore, the BES unit 114 may be configured to identify/segment one or more tissue classes in the anatomical region being imaged based on the corrected intensity image and the updated body mask. Additionally, the BES unit 114 may be configured to generate tissue classified image(s) that depict the segmented tissues.

The system 100 provides a framework that supports simultaneous bias estimation, intensity correction, and segmentation of multiple tissue classes in whole body MRI image data, as desired by PET-MR imaging. Moreover, the system is also agnostic to MRI field strength and coil selection as long as initial bias estimate is robust. Furthermore, the framework provides a robust segmentation of MRI data that is resilient to with broad range of image intensity shading artifacts. The system also obviates the need for "retuning" the segmentation techniques for specific cohorts of image data acquisition and aids in the generation of robust magnetic resonance attenuation correction (MRAC) maps across a wide range of MRI data.

In addition, the BES unit 114 may be accessed and/or operated via an operator console 116. The operator console 116 may also be employed to facilitate visualization of one or more of the tissue classified images, the corrected intensity image, the revised bias map, and the updated body mask generated by the BES unit 114 on a display such as display 118 and/or a printer 120. For example, an operator may use the operator console 116 to designate the manner in which the tissue classified images are visualized on the display 118. Moreover, one or more of the MR image data 104, the PET image data 108, the tissue classified images, the corrected intensity image, the revised bias map, and the updated body mask may be stored in a data repository 122. The working of the system 100 will be described in greater detail with reference to FIGS. 2-6.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present system 100 is provided by way of example, and the present specification is in no way limited by the specific system configuration.

Figure 2:
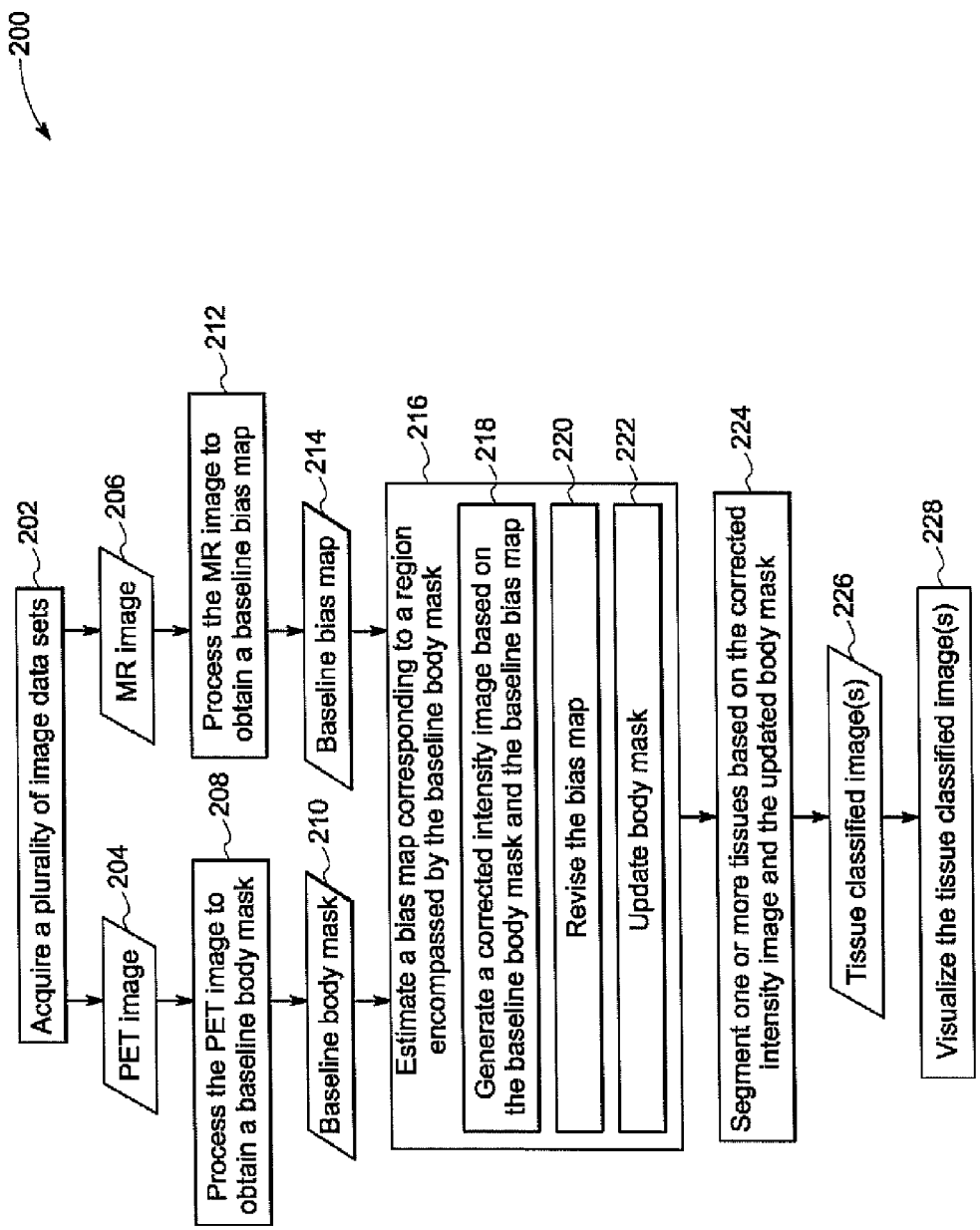
FIG. 2 is a flow chart depicting an exemplary method for image intensity bias estimation and tissue segmentation, in accordance with aspects of the present specification.

Turning now to FIG. 2, a flow chart 200 of exemplary logic for a method for joint image intensity bias estimation and segmentation of tissues using a plurality of anatomically matched image data sets, for example, is depicted. As previously noted, the anatomically matched image data sets may correspond to an anatomical region in a patient acquired by a corresponding imaging system. In the example of FIG. 2, the method 200 is described in terms of a first image data set acquired via a first imaging system and a second image data set acquired via a second imaging system, where the second imaging system is different from the first imaging system. In particular, in the example of FIG. 2, the first image data set includes MR image data, while the second image data set includes PET image data. However, in certain other examples, the second image data set may include CT image data and the like. The method of FIG. 2 is described in terms of the various components of FIG. 1.

The method 200 may be described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as a memory, local to the system 100 (see FIG. 1) and in operative association with a processing subsystem such as the BES unit 114. In certain other embodiments, the computer executable instructions may be located in computer storage media, such as memory storage devices, that are removed from the system 100. Moreover, the method 200 of FIG. 2 includes a sequence of operations that may be implemented in hardware, software, or combinations thereof.

As will be appreciated during a PET/MR imaging session, a subject such as a patient is positioned for imaging and the clinician attempts to image a desired anatomical region in the patient. Following any pre-imaging procedures, an anatomical region for imaging may be selected. In one example, the clinician may identify the anatomical region in the patient to be imaged. As previously noted, the anatomical region may include any tissue that can be perfused or a tissue that has a potential for perfusion deficit. Some non-limiting examples of the anatomical regions of interest include the head and neck regions, the lung region, the abdominal region, the pelvic region, or simply the whole body of the patient. In certain other embodiments, the system 100 may be configured to automatically select the anatomical region to be imaged based on the position of the patient in/on the imaging system, for example.

Subsequent to the selection of the anatomical region, a plurality of image data sets corresponding to the desired anatomical region in the patient may be obtained, as depicted by step 202. As previously noted, the plurality of image data sets may be representative of anatomically matched image data sets acquired using two or more imaging systems. In the example of FIG. 2, the method is described with reference to the use of two sets of anatomically matched image data, such as a PET image data set 204 and an MR image data set 206.

In one embodiment, the image data sets may be obtained in real-time. However, in certain other embodiments, previously acquired data may be retrieved from a data repository, such as the data repository 122.

Moreover, the time-series image data obtained at step 202 may include dynamic 2D images, dynamic 3D images, and/or 4D images. In particular, these dynamic images include 2D and/or 3D images acquired over a determined period of time. Further, the determined period of time may include the scan time, for example. The bias map obtained from MRAC data can be used to correct subsequent MRI data acquisitions such as T1 weighted imaging, T2 weighted imaging, diffusion weighted imaging, perfusion weighted imaging, and the like.

In accordance with exemplary aspects of the present specification, information derived from anatomically matched PET and MR image data sets may be employed to enhance the segmentation of tissues/tissue classes in the anatomical region even in the presence of signal inhomogeneity in the MR image data 206.

In particular, information derived from the PET image data 204 may be used to "quantify" and/or enhance the "quality" of correction of the inhomogeneity in the MR image data 206. More specifically, the PET derived information may be used to enhance the robustness of estimation of bias in the MR image data 206. It may be noted that in certain embodiments, the PET image data 204 may be generated from image reconstruction using PET time-of-flight data without attenuation correction (TOF-NAC image). Accordingly, at step 208, the PET image data set 204 may be processed to obtain a baseline or initial body mask. The baseline body mask may be used as an initial estimate of a contour that encompasses the anatomical region of interest. In one embodiment, the PET image data 204 may be processed via an active contour to obtain the baseline body mask. In another embodiment, a determined threshold may be employed to obtain the initial body mask corresponding to the anatomical region. The baseline body mask 210 provides a boundary that aids in ensuring that only bias corresponding to the region encompassed by the baseline body mask 210 in the MR image data 206 is estimated, thereby enhancing the fidelity of a bias map and any ensuing segmentation.

Furthermore, in cases of severe bias or signal inhomogeneity, non-biased portions of the anatomical region tend to appear as background portions. It is therefore desirable to accurately estimate the bias or signal inhomogeneity corresponding to the anatomical region. Use of the bias map and body mask significantly improves the ability to correct any inhomogeneity shading and allows enhanced segmentation. The bias map also aids in labeling body tissue and the background.

Accordingly, as indicated by step 212, the MR image data 206 may be processed to obtain an estimate of an initial bias. To that end, the MR image data 206 may be processed to generate a baseline or initial bias map. In one embodiment, the baseline bias map may be generated by processing the MR image data 206 via a low pass filter. By way of example, the initial estimate of the bias may be obtained by low-pass filtering of the MR image data 206 with a Gaussian kernel (GW-LPF). In another embodiment, the initial bias estimate may be generated via use of a scanner calibration map obtained from low frequency k-space body coil images and low frequency k-space data from surface coil images. The scanner calibration map may be computed using calibration data or sensitivity profiles corresponding to the plurality of coils used in the parallel imaging process. Alternatively, N3/N4 bias field correction may be used to generate the initial bias estimate or map.

As will be appreciated, the MR image data set 206 includes in-phase images ($I_{in}$) and out-phase images ($I_{out}$). These images $I_{in}$ and images $I_{out}$ may be processed to obtain water images ($I_w$) and fat images ($I_f$) using Dixon processing, in one example.

An initial pre-processed image $I_{prep}$ may be generated as:

$$I_{prep} = \text{MAX}(I_f/I_{in}, I_w/I_{in}) \quad (1)$$

Furthermore, an initial estimate of bias $b_{init}$ may be obtained by processing the in-phase image $I_{in}$ via a low pass filter, such as a Gaussian kernel G.

$$b_{init} = I_{in} * G_\sigma \quad (2)$$

where an example value of $\sigma$ is 5 pixels.

In accordance with aspects of the present specification, a multiplicative model may be assumed for image shading. Also, b may be representative of a shading bias map across an imaging field of view (FOV). In particular, $$I_{in(shaded)} = I_{in(true)} * b \quad (3)$$

where $I_{in(shaded)}$ is representative of bias corrupted in-phase data and $I_{in(true)}$ is a true representation of signal intensity obtained from the tissues.

The intensity corrected image may be obtained by dividing the corrupted image by the bias map. Moreover, the initial pre-processed image $I_{prep}$ may be combined with a weighted sum of its gradient image, thereby may be corrected using the bias field. Also, the bias corrected initial pre-processed image may be combined with a weighted sum of its gradient image, thereby enhancing segmentation at a boundary of an image edge.

In accordance with aspects of the present specification, the MR image data 206 may be further processed to segment one or more tissues/tissue classes in the anatomical region of interest. More particularly, the MR image data 206 may be processed employing the baseline body mask 210 and the baseline bias map 214 to estimate a bias map corresponding to a sub-region within the anatomical region, wherein the sub-region is representative of a region encompassed by the baseline bias map. In one embodiment, estimating the bias map may include generating a corrected intensity image, revising the bias map, and updating the body mask, as indicated by steps 218-222.

As noted hereinabove, signal inhomogeneity due to bias such as B1 bias in the MR image data 206 may result in shading artifacts, which adversely affect the accuracy of segmentation of the tissues. By way of example, MR surface coil images show spatially varying contrast due to B1 bias, thereby necessitating correction of bias field related contrast changes. Accordingly, it is desirable to estimate a bias corresponding to the anatomical region and correct the estimated bias to circumvent the adverse effects of the shading artifacts on the segmentation of the tissues in the anatomical region.

According to aspects of the present specification, a framework that allows the simultaneous iterative updating of the bias field and segmentation using a phase field approach is presented. In particular, the estimation and correction of the bias field and the segmentation of the tissues in the anatomical region may be expressed using a two-class phase-field formulation to generate the body mask and bias map. One example of the two-class phase-field formulation is presented in equation (4).

$$E[u,b] = \int_\Omega (1-u)^2 \left(\frac{I_{prep}}{b+\varepsilon} - c_{air}\right)^2 dx + \int_\Omega u^2 \frac{\alpha}{1+\beta\left(\frac{I_{prep}}{b+\varepsilon} - c_{air}\right)^2} dx + \tilde\lambda \int_\Omega u^2(1-u)^2 dx + \lambda \int_\Omega |\nabla u|^2 dx + \lambda_b \int_\Omega |\nabla b|^2 dx + \tilde\lambda_b \int_\Omega (b - b_{init})^2 dx \quad (4)$$

In equation (4), E is representative of energy, where the energy is minimized over binary indicator functions $u(x) \in \{0, 1\}$, where $u(x)=0$ is indicative of an air pixel or background pixel and $u(x)=1$ is indicative of a non-air pixel or body pixel. Also, b is representative of the bias of the MR image data 206.

Accordingly, at step 216, the MR image data 206 may be processed based on the formulation of equation (4) to estimate a bias map or field based on the baseline body mask 210 and the baseline bias map 214. In equation (4), E is representative of the energy to be minimized, u is representative of a body mask, and b is representative of a bias map.

Furthermore, term 1

$$\left(\int_\Omega (1-u)^2 \left(\frac{I_{prep}}{b+\varepsilon} - c_{air}\right)^2 dx\right)$$

of equation (4) is used to seek image intensity close to that of the background, $c_{air}$ in the region where the body mask $u=0$. Also, term 2

$$\left(\int_\Omega u^2 \frac{\alpha}{1+\beta\left(\frac{I_{prep}}{b+\varepsilon} - c_{air}\right)^2} dx\right)$$

of equation (4) is used to seek image intensity that is different from that of the background, $c_{air}$ in the region where the body mask $u=1$. Moreover, term 3

$$\left(\tilde\lambda \int_\Omega u^2(1-u)^2 dx\right)$$

of equation (4) is used to constrain u to be $\{0, 1\}$, while term 4

$$\left(\lambda \int_\Omega |\nabla u|^2 dx\right)$$

of equation (4) is representative of a smoothing term for the body mask u. Also, term 5

$$\left(\lambda_b \int_\Omega |\nabla b|^2 dx\right)$$

of equation (4) is a smoothing term for the bias map b and term 6

$$\left(\tilde\lambda_b \int_\Omega (b - b_{init})^2 dx\right)$$

of equation (4) is used for bias correction, where $b_{init}$ is the initial estimate of the bias (for example, the baseline bias map 214). Also, parameters $\alpha$, $\beta$, and $\lambda$ respectively relate to noise variance, smoothness and sensitivity. In particular, $\beta$ relates to the standard deviation of the background distribution, while $\lambda$ captures the scale of the segmentation used to produce an accurate body contour. Moreover, in certain embodiments, values of these parameters may be manually set.

In accordance with aspects of the present specification, equation (4) may be iteratively solved for the body mask u and the bias map b. It may be noted an initial value $u_0$ may be representative of the baseline body mask 210, while an initial value $b_0$ may be representative of the baseline bias map 214. Moreover, the Euler Lagrange expression of equation (4) is a semi-linear partial differential equation. The energy E may be minimized using a steepest descent method, for example. The descent equation may be solved using a finite differences based semi-implicit iterative method in a multi-resolution framework. In one example, the iterative scheme may be split into two parts. In accordance with the first part of the iterative scheme, the body mask u may be updated based on contributions from terms 1, 2, 4, 5, 6 of equation (4). Subsequently, effects of term 3 may be considered. In this situation, since equation (4) is a linear PDE, finite differences based implicit schemes may be utilized for fast and stable convergence. Alternatively, in accordance with a second part of the iterative scheme, the iterative scheme may be implemented through thresholding the body mask u such that the value of the body mask lies in {0, 1} after each iteration.

Consequent to the processing the MR image data set 206 based on the baseline body mask 210 and the baseline bias map 214, bias corresponding to the region encompassed by the baseline body mask 210 may be estimated. Subsequently, at step 218, MR image data corresponding to the region encompassed by the baseline body mask 210 may be corrected based on the bias estimated at step 216. Furthermore, at step 220, the baseline bias map 214 may be revised to generate a revised bias map. The revised bias map may correspond to the corrected intensity image data generated at step 218. Additionally, the baseline body mask 210 may be updated to generate an updated body mask or contour, as indicated by step 222. Steps 216-222 may be iteratively repeated until the energy E of equation (4) is minimized.

In addition, at step 224, tissues/tissue classes internal to the anatomical region may be segmented. In particular, the corrected intensity image data and the updated body mask respectively generated at steps 218 and 222 may be used to segment the tissues in the anatomical region. Accordingly, one or more robust tissue classified images 226 may be generated.

Optionally, the images 226 may be communicated to a user such as a clinician, as indicated by step 228, for example. In one example, the tissue classified images 226 may be visualized on a display, such as the display 118 of FIG. 1. Also, these images 226 may be stored in a data repository such as the data repository 122 of FIG. 1.

Use of PET derived information results in a robust estimation of the bias. In particular, use of the PET derived information aids in quantifying the level of inhomogeneity and therefore permits adjustment of parameters used in the estimation of the initial bias estimate (for example, N3/N4 parameters such as full width half max stopping criterion, resampling factor, number of iterations, and the like) or the final bias estimation (for example, joint bias parameters such as weight of the bias field ($\lambda_{bias}$). Moreover, use of the body mask derived from the PET image data 204 aids in providing a search region (for example, region encompassed by the PET body mask) for bias estimation. Additionally, PET images are not affected by metallic implants and therefore provide an accurate depiction of the body contour even in the presence of surface implants. Also, the PET derived search region is used to ensure that the bias estimation is confined to the PET derived search region only, thereby enhancing the fidelity of the bias map and ensuing segmentation of the tissue classes. Additionally, the use of PET information makes the technique robust to variations that arise due to use of different coils/field strengths. The method of FIG. 2 supports the simultaneous estimation and correction of bias and enhanced segmentation of one or more tissues in the anatomical region being imaged.

Figures 3A, 3B, 3C:
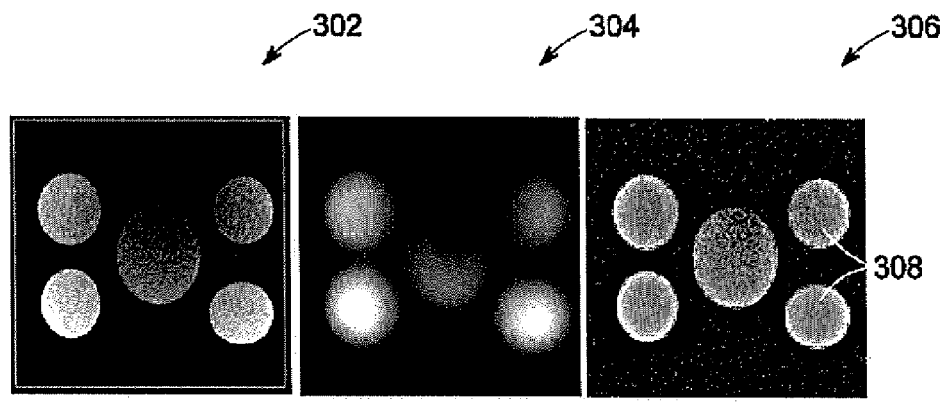
FIGS. 3A, 3B, and 3C are diagrammatical representations of an example the joint image intensity bias estimation and tissue segmentation of FIG. 2, in accordance with aspects of the present specification.

FIGS. 3(A)-3(C) are diagrammatical representation of one example of the joint bias field estimation and segmentation method 200 of FIG. 2. In particular, FIG. 3(A) depicts an MR image data 302 that is received as input by the system 100 and processed by the BES unit 114 in particular. Also, a bias map 304 corresponding to the MR image data set 302 computed by the BES unit 114 is depicted in FIG. 3(B). Furthermore, FIG. 3(C) depicts an image of a corrected intensity image 306. Reference numeral 308 is representative of segmented tissues 308. The example of FIGS. 3(A)-3(C) demonstrates the robust segmentation of the tissues 308 in the anatomical region of interest even in the presence of noise (see FIG. 3(A)) and shading across the image (see FIG. 3(B)) using the joint bias estimation and segmentation method 200 of FIG. 2.

Figures 4A, 4B, 4C:
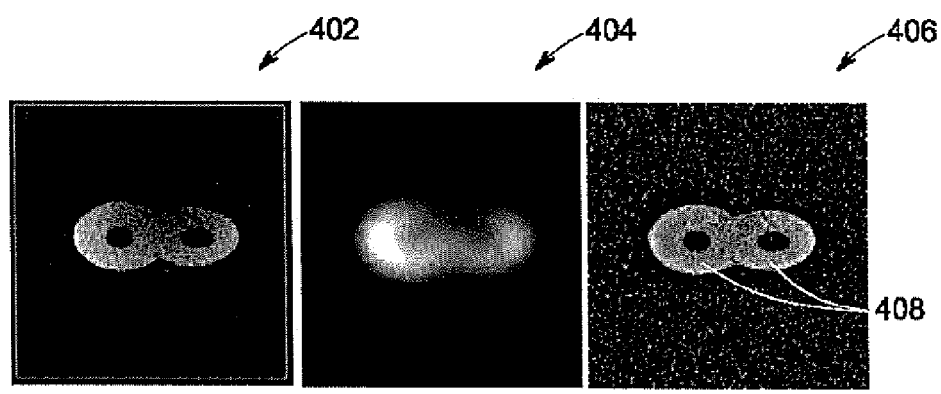
FIGS. 4A, 4B, and 4C are diagrammatical representations of another example the joint image intensity bias estimation and tissue segmentation of FIG. 2, in accordance with aspects of the present specification.

Referring now to FIGS. 4(A)-4(C), diagrammatical representations of another example of the joint bias field estimation and segmentation method 200 of FIG. 2 are presented. FIG. 4(A) depicts an MR image data set 402 that is received as input by the system 100 and the BES unit 114 in particular, for example. Also, reference numeral 404 is representative of a bias map 404 corresponding to the MR image data set 402 computed by the BES unit 114. Furthermore, FIG. 4(C) depicts an image 406 that is representative of a corrected intensity image, while reference numeral is representative of segmented tissues 408. The example of FIGS. 4(A)-4(C) demonstrates the robust segmentation of the tissues in the anatomical region of interest even in the presence of noise (see FIG. 4(A)) and shading across the image (see FIG. 4(B)) using the joint bias estimation and segmentation framework presented hereinabove.

Figures 5A, 5B:
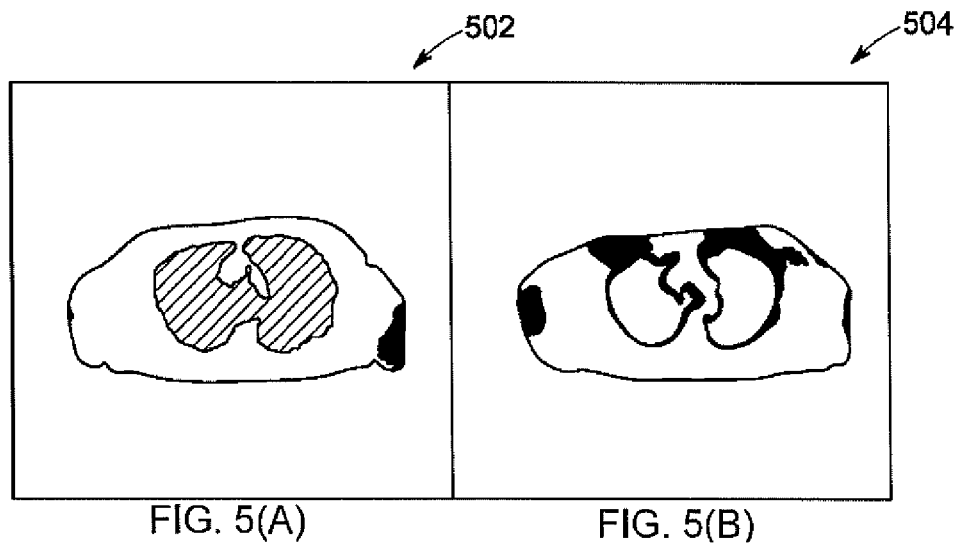
FIGS. 5A and 5B are diagrammatical representations of an example of tissue segmentation without bias correction via use of currently available techniques.

Turning now to FIGS. 5(A)-5(B) are representative of segmentation of MR image data using currently available techniques. FIG. 5(A) depicts an MR image data set 502. As depicted in FIG. 5(A), there exist shading artifacts across the image 502 due to use of surface coils in the acquisition of the image data. FIG. 5(B) depicts the segmentation 504 of the image 502 using currently available techniques. It may be noted that the processing of the image data 502 using presently available techniques without bias correction results in severe under-segmentation or failure of segmentation of the tissues.

Figures 6A, 6B:
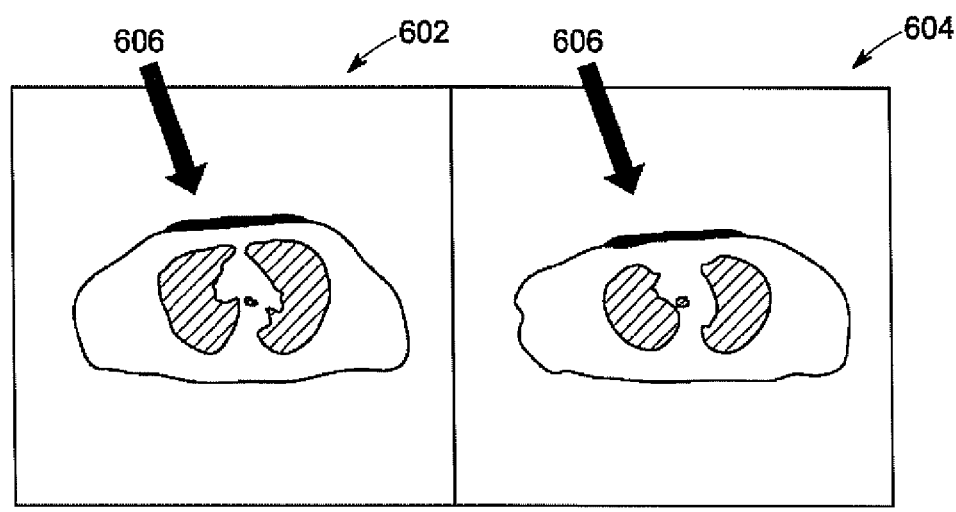
FIGS. 6A and 6B are diagrammatical representations of an example of tissue segmentation with bias correction via use of the method for joint image intensity bias estimation and tissue classification of FIG. 2, in accordance with aspects of the present specification.

FIG. 6(A)-6(B) are representative of segmentation of MR image data using the systems and methods of the present specification. In particular, FIG. 6(A) is representative of a bias corrected image 602, in accordance with aspects of the present specification. Moreover, FIG. 6(B) is representative of an image 604 that has been processed in accordance with the method 200 presented in FIG. 2. It may be observed from FIG. 6(B) that the intensity image is uniform throughout the FOV and also results in enhanced segmentation of the tissues even in the presence of ghosting artifacts 606.

The bias map obtained from the MRAC data is specific to the coil and the anatomy being examined. Accordingly, any further MRI acquisitions (for example, DWI imaging, PWI imaging, T1-weighted imaging, and T2-weighted imaging) of the same anatomy and using similar coils can utilize the same bias map. Additionally, intensity shading in these acquisitions can also be corrected by simply matching the bias map to the acquisition geometry (for example, FOV, matrix size and orientation).

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The various systems and methods for the joint estimation/correction of image intensity bias and segmentation of tissue classes presented hereinabove provide a framework for robust estimation/correction of the spatial signal bias introduced by RF transmission and coils and segmentation of the tissue classes of Dixon MRI images within the phase field based framework. The framework provides robust segmentation of MRI data that is resilient to a broad range of image intensity shading artifacts. Also, use of the systems and methods presented herein obviates the need to "retune" the segmentation techniques for specific cohort of data acquisition obtained at different field strengths and coil configurations.

Moreover, use of PET derived information to "quantify" and enhance the "quality" of shading correction enhances the estimation of the bias map and in turn improves the quality of segmentation of the tissues. Furthermore, the methods presented herein are also agnostic to MRI field strengths and coil selection. In cases of severe inhomogeneity, typically observed in imaging below pelvis, the use of a bias map significantly enhances the quality of correction of inhomogeneity shading and results in improved segmentation. In addition, the PET derived search region guides the estimation of the bias, thereby improving the fidelity of the bias map and the segmentation.

The systems and methods of the present specification allow magnetic resonance attenuation correction (MRAC) data acquisition with surface coils, thereby resulting in a faster acquisition workflow for a PET-MR system. Moreover, data redundancy is reduced since the same high resolution scan acquired via a surface coil can also be used for anatomical referencing of PET images. Furthermore, the systems and methods also obviate the need for separate, independent intensity correction of the MRI data with surface coils followed by segmentation, thereby simplifying the clinical workflow. In addition, the systems and methods provide for parameter independent body contour segmentation across data obtained from different coils and thereby results in a simplified workflow for PET-MR attenuation map generation.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

What is claimed is:

1. A method for estimating image intensity bias and segmenting tissues, the method comprising:
   obtaining a first image data set and at least a second image data set, wherein the first image data set and the second image data set are representative of an anatomical region in a subject of interest;
   generating a baseline bias map by processing the first image data set;
   determining a baseline body mask by processing the second image data set;
   estimating a bias map corresponding to a sub-region in the anatomical region based on the baseline body mask; and
   segmenting one or more tissues in the anatomical region based on the bias map.

2. The method of claim 1, wherein the first image data set is acquired using a first imaging system, wherein the second image data set is acquired using a second imaging system, and wherein the second imaging system is different from the first imaging system.

3. The method of claim 1, wherein generating the baseline bias map comprises processing the first image data set via a low pass filter, a calibration map, a retrospective bias field corrected map, or combinations thereof.

4. The method of claim 1, wherein the baseline body mask encompasses the anatomical region.

5. The method of claim 1, wherein determining the baseline body mask comprises processing the second image data set via an active contour, a determined threshold, or a combination thereof.

6. The method of claim 1, wherein estimating the bias map further comprises:
   generating a corrected intensity image based on the baseline body mask and the bias map;
   revising the bias map to generate a revised bias map; and
   updating the baseline body mask to obtain an updated body mask.

7. The method of claim 6, further comprising iteratively updating one or more of the corrected intensity image, the revised bias map, and the updated body mask.

8. The method of claim 7, wherein iteratively updating one or more of the corrected intensity image, the revised bias map, and the updated body mask comprises using a two-class phase-field formulation.

9. The method of claim 6, wherein segmenting the one or more tissues comprises segmenting the one or more tissues based on the corrected intensity image and the updated body mask.

10. The method of claim 9, further comprising visualizing one or more of the corrected intensity image, the revised bias map, the updated body mask, and the one or more segmented tissues on a display.

11. The method of claim 1, further comprising processing other acquisitions of the first image data set by the bias map, wherein the subsequent acquisitions of the first image data set correspond to the anatomical region.

* * * * *